US009388274B2

(12) United States Patent
Owusu-Adom et al.

(10) Patent No.: US 9,388,274 B2
(45) Date of Patent: Jul. 12, 2016

(54) MERCAPTO-CONTAINING BISANHYDROHEXITOL DERIVATIVES AND USES THEREOF

(71) Applicant: 3M INNOVATIVE PROPERTIES COMPANY, St. Paul, MN (US)

(72) Inventors: Kwame Owusu-Adom, Stone Mountain, GA (US); Kevin M. Lewandowski, Inver Grove Heights, MN (US); Jonathan E. Janoski, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 232 days.

(21) Appl. No.: 14/364,398

(22) PCT Filed: Dec. 7, 2012

(86) PCT No.: PCT/US2012/068410
§ 371 (c)(1),
(2) Date: Jun. 11, 2014

(87) PCT Pub. No.: WO2013/090138
PCT Pub. Date: Jun. 20, 2013

(65) Prior Publication Data
US 2014/0350196 A1    Nov. 27, 2014

Related U.S. Application Data

(60) Provisional application No. 61/576,584, filed on Dec. 16, 2011.

(51) Int. Cl.
*C08G 59/66* (2006.01)
*C07D 493/04* (2006.01)

(52) U.S. Cl.
CPC .............. *C08G 59/66* (2013.01); *C07D 493/04* (2013.01)

(58) Field of Classification Search
CPC ...................................... C08G 59/66
See application file for complete search history.

(56) References Cited

U.S. PATENT DOCUMENTS

| 3,272,845 | A | 9/1966 | Zech |
| 4,552,798 | A | 11/1985 | Ryoke |
| 4,778,851 | A | 10/1988 | Henton |
| 5,292,903 | A | 3/1994 | Conner |
| 5,498,675 | A | 3/1996 | Emmons |
| 5,629,380 | A | 5/1997 | Baldwin |
| 6,395,810 | B1 | 5/2002 | Luitjes |
| 6,608,167 | B1 | 8/2003 | Hayes |
| 6,632,872 | B1 | 10/2003 | Pellerite |
| 7,365,148 | B2 | 4/2008 | Ono |
| 7,713,326 | B2 | 5/2010 | Carstens |
| 7,910,666 | B2 | 3/2011 | Byers |
| 2003/0026922 | A1 | 2/2003 | May |
| 2005/0004270 | A1 | 1/2005 | Rocks |
| 2005/0197390 | A1 | 9/2005 | Byers |
| 2006/0009365 | A1 | 1/2006 | Erhan |
| 2006/0235052 | A1 | 10/2006 | Moliner |
| 2007/0112100 | A1 | 5/2007 | Byers |
| 2010/0130759 | A1 | 5/2010 | Gillet |
| 2013/0217804 | A1 | 8/2013 | Campbell |
| 2013/0225725 | A1 | 8/2013 | Campbell |
| 2016/0016969 | A1* | 1/2016 | Stensrud ............... C07D 519/00 549/464 |

FOREIGN PATENT DOCUMENTS

| CN | 1876740 | 12/2006 |
| CN | 102140219 | 8/2011 |
| EP | 0942028 | 9/1999 |
| IN | 2010-CH03359 | 7/2012 |
| JP | 2009-046402 | 3/2009 |
| WO | WO 99/36484 | 7/1999 |
| WO | WO 2009/023759 | 2/2009 |
| WO | WO 2013/090136 | 6/2013 |

OTHER PUBLICATIONS

Bachmann, "Synthesis of Novel Polyurethanes and Polyureas by Polyaddition Reactions of Dianhydrohexitol Configurated Diisocyanates", Macromolecular Chemistry and Physics, Nov. 2001, vol. 202, Issue 17, pp. 3410-3419.
Wardell, J.L. (1974). Preparation of Thiols. In S. Patai (Ed.), *The Chemistry of the Thiol Group*: Part 1 (Chapter 4, pp. 169-270). London: John Wiley & Sons.
Cawse, "Polymers from renewable sources, 1. Diamines and diisocyanates containing difurylalkane moieties", Makromol. Chem., 1984, vol. 185, pp. 697-707.
Roberts, "Thiols", Kirk-Othmer Encyclopedia of Chemical Technology, 2003, John Wiley & Sons, Inc., 15 pgs.
Edward M. Petrie, Epoxy Adhesive Formulations, pp. 107-110 (2006).
International Search Report for PCT International Application No. PCT/US2012/068410, mailed on Feb. 13, 2013, 4pgs.

* cited by examiner

*Primary Examiner* — Megan McCulley
(74) *Attorney, Agent, or Firm* — Jean A. Lown

(57) ABSTRACT

Bisanhydrohexitol derivatives having terminal mercapto groups are provided. Additionally, curable compositions that include these mercapto-containing bisanhydrohexitol derivatives, cured compositions prepared from the curable compositions, and articles containing the cured compositions are provided. More specifically, the curable compositions are epoxy-based formulations and the mercapto-containing bisanhydrohexitol derivatives function as curing agents for epoxy resins.

15 Claims, No Drawings

MERCAPTO-CONTAINING BISANHYDROHEXITOL DERIVATIVES AND USES THEREOF

CROSS REFERENCE TO RELATED APPLICATIONS

This application is a national stage filing under 35 U.S.C. 371 of PCT/US2012/068410, filed Dec. 7, 2012, which claims priority to U.S. Provisional Application No. 61/576,584, filed Dec. 16, 2011, the disclosure of which is incorporated by reference in its/their entirety herein.

TECHNICAL FIELD

Mercapto-containing bisanhydrohexitol derivatives and the use of these derivative compounds in both curable and cured compositions are described.

BACKGROUND

Mercaptan compounds have been used as curatives for epoxy resins. However, like many reactants used in the preparation of various polymeric materials, most known mercaptan compounds are prepared from petroleum-based feedstocks. Current consumer demands, regulatory considerations, and dwindling sources of petroleum-based raw materials have created a need for alternative sources of materials as feedstocks the preparation of polymeric materials.

Some plant-based mercaptan compounds are known. For example, soybean oil has been mercaptanized as described in U.S. Pat. No. 7,910,666 (Byers et al.), U.S. Pat. No. 7,713,326 (Carstens et al.), and U.S. Patent Application Publication 2005/0197390 A1 (Byers et al.).

Various derivatives of bisanhydrohexitols (i.e., derivatives of isosorbide, isomannide, isoidide, or a mixture thereof) are known. For example, U.S. Pat. No. 6,608,167 (Hayest et al.) describes the use of bis(2-hydroxyethyl)isosorbide as a monomer in the preparation of various polyesters. U.S. Patent Application Publication 2010/0130759 (Gillet) describes various bisanhydrohexitol derivatives with terminal —CH$_2$NH$_2$ groups that can be used as monomers in the preparation of polyamides. U.S. Pat. No. 7,365,148 (Ono et al.) describes a polycarbonate prepared from bisanhydrohexitol. Isosorbide diglycidyl ethers are described in U.S. Pat. No. 3,272,845 (Zech et al.).

SUMMARY

Bisanhydrohexitol derivatives (i.e., isosorbide derivatives, isomannide derivatives, isoidide derivatives, or mixtures thereof) having two terminal mercapto groups are provided. Additionally, curable compositions that include these mercapto-containing bisanhydrohexitol derivatives, cured compositions prepared from the curable compositions, and articles containing the cured compositions are provided. More specifically, the curable compositions are epoxy-based formulations. The cured compositions can be used, for example, as a structural adhesive or as a coating.

In a first aspect, a bisanhydrohexitol derivative with two terminal mercapto groups is provided. These mercaptan compounds are of Formula (I).

HS-L-Y—O-Q-O—Y-L-SH (I)

In Formula (I), each group Y is independently a single bond or a carbonyl and each group L is independently an alkylene or heteroalkylene. Group Q is a divalent group of Formula (I-1), (I-2), or (I-3).

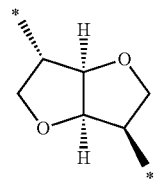
(I-1)

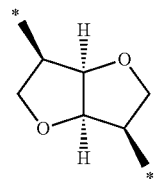
(I-2)

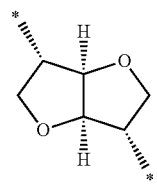
(I-3)

The asterisk indicates the attachment points of the divalent group Q to the rest of the compound of Formula (I).

In a second aspect, a curable composition is provided that includes (a) an epoxy resin and (b) a first curing agent. The first curing agent is a mercaptan compound of Formula (I) as described above.

In a third aspect, an article is provided that includes a first substrate and a cured composition positioned adjacent to the first substrate. The cured composition contains a reaction product of a curable composition that includes (a) an epoxy resin and (b) a first curing agent. The first curing agent is a mercaptan compound of Formula (I) as described above.

The above summary of the present invention is not intended to describe each embodiment or every implementation of the present invention. The Detailed Description and Examples that follow more particularly exemplify these embodiments.

DETAILED DESCRIPTION OF THE INVENTION

Bisanhydrohexitol derivatives having two terminal mercapto groups are provided. Curable compositions that include these mercapto-containing bisanhydrohexitol derivatives (i.e., mercaptan compounds) are also provided. More specifically, the curable compositions are epoxy-based formulations and the mercapto-containing bisanhydrohexitol derivatives function as curing agents for epoxy resins. Additionally, cured compositions prepared from the curable compositions and articles that include the cured compositions are provided. The cured compositions can be used, for example, as a structural adhesive or as a coating.

In a first aspect, mercaptan compounds of Formula (I) are provided.

HS-L-Y—O-Q-O—Y-L-SH (I)

In Formula (I), each group Y is independently a single bond or a carbonyl and each group L is independently an alkylene or heteroalkylene. The group Q is a divalent group of Formula (I-1), (I-2), or (I-3).

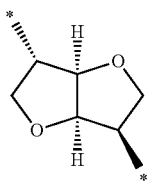
(I-1)

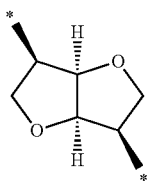
(I-2)

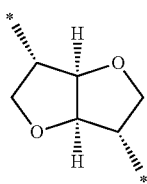
(I-3)

The asterisks indicate the attachment points of the divalent group Q to the rest of the compound of Formula (I). In the mercaptan compounds of Formula (I), the two Y groups, the two L groups, and the two —O—Y-L-SH groups can be the same or different.

As used herein, the term "mercaptan" refers to a compound having one or more mercapto groups. A mercapto is a monovalent group —SH. The mercaptan compounds of Formula (I) have two mercapto groups.

The mercaptan compounds are mercapto-containing bisanhydrohexitol derivatives. There are three stereoisomers of bisanhydrohexitol: isosorbide, isomannide, and isoidide. When group Q is of Formula (I-1), the mercaptan compounds of Formula (I) are isosorbide derivatives of Formula (IA).

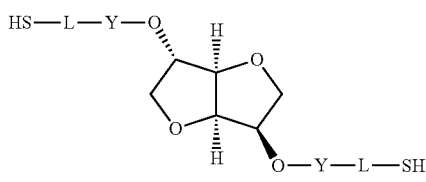
(IA)

When group Q is of Formula (I-2), the mercaptan compounds of Formula (I) are isomannide derivatives of Formula (IB).

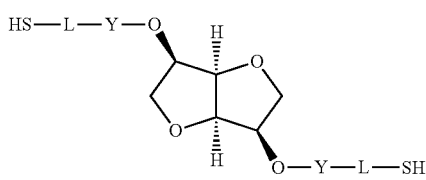
(IB)

When group Q is of Formula (I-3), the mercaptan compounds of Formula (I) are isoidide derivatives of Formula (IC).

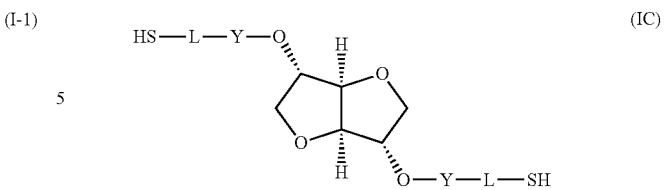
(IC)

The mercaptan compounds of Formula (IA), Formula (IB), and Formula (IC) are stereroisomers. Each stereoisomer can be present individually or in a mixture with one or more of the other stereoisomers.

When group Y in Formula (I) is a carbonyl group, the mercaptan compounds are of Formula (II).

HS-L-(CO)—O-Q-O—(CO)-L-SH    (II)

As used herein, the term "carbonyl" refers to the divalent group —(CO)— where the carbon and oxygen atoms are connected by a double bond. The mercaptan compounds of Formula (II) are esters containing two groups of formula —O(CO)-L-SH.

When group Y in Formula (I) is a single bond, the mercaptan compounds are of Formula (III).

HS-L-O-Q-O-L-SH    (III)

The mercaptan compounds of Formula (III) are ethers containing two groups of formula O-L-SH.

In some versions of Formulas (I), (II), and (III), group L is an alkylene. As used herein, the term "alkylene" refers to a divalent group that is a radical of an alkane. The alkylene can be straight-chained, branched, cyclic, bicyclic, or a combination thereof. The alkylene typically has 1 to 30 carbon atoms. In some embodiments, the alkylene contains 1 to 20 carbon atoms, 1 to 10 carbon atoms, 1 to 6 carbon atoms, 1 to 4 carbon atoms, or 1 to 3 carbon atoms. The radical centers of the alkylene can be on the same carbon atom (i.e., an alkylidene) or on different carbon atoms.

In other versions of Formulas (I), (II), and (III), group L is a heteroalkylene. As used herein, the term "heteroalkylene" refers to a divalent alkylene having one or more —CH$_2$— groups replaced with a thio (—S—), oxy (—O—), or —NR$^a$— where R$^a$ is hydrogen or alkyl. The heteroalkylene can be linear, branched, cyclic, bicyclic, or a combination thereof and can include up to 30 carbon atoms and up to 20 heteroatoms. In some embodiments, the heteroalkylene includes up to 20 carbon atoms and up to 12 heteroatoms, up to 10 carbon atoms and up to 6 heteroatoms, up to 6 carbon atoms and up to 4 heteroatoms, or up to 4 carbon atoms and up to 3 heteroatoms. Suitable R$^a$ alkyl groups typically have 1 to 10 carbon atoms, 1 to 6 carbon atoms, or 1 to 4 carbon atoms.

When group L is a heteroalkylene, the one or more heteroatoms are often oxygen atoms (i.e., the heteroalkylene contains one or more oxy groups) and group L is an ether group or polyether group. Some example compounds of Formula (I) have a heteroalkylene group L with a single oxy group as shown in the compounds of Formula (IV).

HS-L$^2$-O-L$^1$-Y—O-Q-O—Y-L$^1$-O-L$^2$-SH    (IV)

The heteroalkylene group L in Formula (I) is the ether group of -L$^1$-O-L$^2$- in Formula (IV). Each group L$^1$ and L$^2$ is an alkylene group having 1 to 10 carbon atoms, 1 to 6 carbon atoms, or 1 to 4 carbon atoms.

Example compounds of both Formulas (I) and (II) include, but are not limited to, HS—CH$_2$—(CO)—O-Q-O—(CO)—CH$_2$—SH, HS—CH(CH$_3$)—(CO)—O-Q-O—(CO)—CH(CH$_3$)—SH, and HS—CH$_2$CH$_2$—(CO)—O-Q-O—(CO)—

$CH_2CH_2$—SH. Group Q can be of Formula (I-1), (I-2), or (I-3). In some embodiments, group Q is of Formula (I-1) and the mercaptan compounds of Formula (I) and (II) are isosorbide derivatives.

An example compound of both Formulas (I) and (III) includes, but is not limited to, HS—$CH_2CH_2CH_2$—O-Q-O—$CH_2CH_2CH_2$—SH. Group Q can be of Formula (I-1), (I-2), or (I-3). In some embodiments, group Q is of Formula (I-1) and the mercaptan compounds of Formula (I) and (III) are isosorbide derivatives.

The mercaptan compounds of Formula (II) that are esters can be prepared using any method known in the art. For example, a single step synthesis method such as that shown in Reaction Scheme A can be used.

Reaction Scheme A

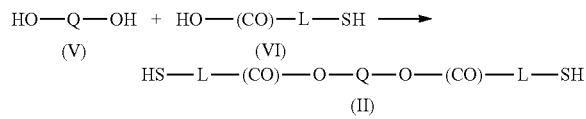

Using this synthesis method, bisanhydrohexitol of Formula (V) is reacted with a compound of Formula (VI). Some example compounds of Formula (VI) include, but are not limited to, mercaptoacetic acid where L is equal to —$CH_2$—, 2-mercaptopropionic acid where L is equal to —$CH(CH_3)$—, 3-mercaptopropionic acid where L is equal to —$CH_2CH_2$—, 3-mercaptoisobutyric acid where L is equal to —$CH(CH_3)CH_2$—, 4-mercaptobutyric acid where L is equal to —$CH_2CH_2CH_2$—, and 4-mercaptopentanoic acid where L is equal to —$CH_2CH_2CH(CH_3)$—. A strong acid catalyst such as sulfuric acid, p-toluene sulfonic acid, or methane sulfonic acid is typically used in this synthesis method.

The mercaptan compounds of Formula (III) that are ethers can be prepared using any method known in the art. For example, a method such as that shown in Reaction Scheme B can be used.

Reaction Scheme B

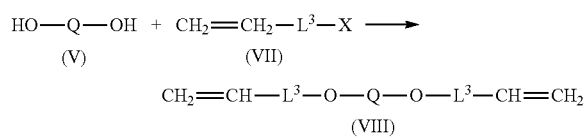

-continued

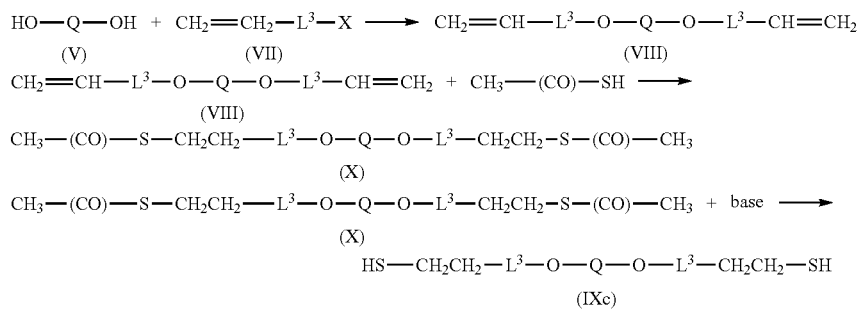

In this reaction scheme, an unsaturated halide compound of Formula (VII) is reacted initially with bisanhydrohexitol of Formula (V) to provide an intermediate compound of Formula (VIII). Suitable compounds of Formula (VII) include those where $L^3$ is an alkylene having 1 to 12 carbon atoms, 1 to 10 carbon atoms, 1 to 8 carbon atoms, 1 to 6 carbon atoms, or 1 to 4 carbon atoms. Group X in Formula (VII) is a halo such as bromo, chloro, or iodo. For example, the compound of Formula (VII) can be allyl bromide or allyl chloride where $L^3$ is a —$CH_2$— group. The intermediate compound of Formula (VIII) is then reacted with hydrogen sulfide. A mixture of three isomeric products (compounds of Formula IXa, IXb, and IXc) is typically obtained. The group L in Formula (I) and (III) is equal to group -$L^3$-$CH_2CH_2$— or -$L^3$-$CH(CH_3)$— in the products of Formulas (IXa) to (IXc). This type of reaction is further described, for example, in Patai, S., *The Chemistry of the Thiol Group*, Part 1, Wiley, New York, pp 169-269 (1974).

Alternatively, Reaction Scheme C can be used to synthesize the mercaptan compounds of Formula (III) are ethers. With this reaction scheme, the product is usually a single isomer of Formula (IXc).

Reaction Scheme C $$HO—Q—OH + CH_2{=}CH_2—L^3—X \longrightarrow CH_2{=}CH—L^3—O—Q—O—L^3—CH{=}CH_2$$
$$(V) \quad\quad (VII) \quad\quad\quad\quad (VIII)$$
$$CH_2{=}CH—L^3—O—Q—O—L^3—CH{=}CH_2 + CH_3—(CO)—SH \longrightarrow$$
$$(VIII)$$
$$CH_3—(CO)—S—CH_2CH_2—L^3—O—Q—O—L^3—CH_2CH_2-S—(CO)—CH_3$$
$$(X)$$
$$CH_3—(CO)—S—CH_2CH_2—L^3—O—Q—O—L^3—CH_2CH_2-S—(CO)—CH_3 + base \longrightarrow$$
$$(X)$$
$$HS—CH_2CH_2—L^3—O—Q—O—L^3—CH_2CH_2—SH$$
$$(IXc)$$

As with Reaction Scheme B, a compound of Formula (VII) is reacted initially with bisanhydrohexitol of Formula (V) to provide a first intermediate compound of Formula (VIII). Suitable compounds of Formula (VII) are the same as described above for Reaction Scheme B. The first intermediate of Formula (VIII) is then reacted with thioacetic acid ($CH_3$—(CO)SH) to form the second intermediate of Formula (X). This second intermediate of Formula (X) can be deprotected by reaction with a strong base such as sodium hydroxide to provide the product of Formula (IXc). The group L in Formula (I) and (III) is equal to group -$L^3$-$CH_2CH_2$— in the product of Formula (IXc). This type of reaction is further described, for example, in Patai, S., *The Chemistry of the Thiol Group*, Part 1, Wiley, New York, pp 169-269 (1974).

As shown in Reaction Schemes A, B, and C, all of the various compounds of Formula (I) are based on the use of a bisanhydrohexitol of Formula (V). A single steroisomer or a mixture of stereoisomers of Formula (V) can be used in any of these reaction schemes. The various stereoisomers of bisanhydrohexitol are typically prepared from sugars such as those from corn starch. For example, isosorbide can be formed from D-glucose (e.g., by hydrogenation followed by dehydration with an acid catalyst), isomannide can be formed from D-mannose, and isoidide can be formed from L-idose. The use of plant-based feedstocks rather than petroleum-based feedstocks can be desirable for many applications. That is, in contrast to petroleum-based feedstocks, plant-based feedstocks are renewable.

The compounds of Formula (I) are typically liquids at room temperature. Stated differently, the compounds of Formula (I) are not liquid crystals at room temperature.

In another aspect, curable compositions are provided that contain a) an epoxy resin and b) a curing agent that includes a mercaptan compound of Formula (I). The curable compositions are typically applied as a coating composition to at least one surface of a substrate and then cured. In other embodiments, the cured compositions can be used as structural adhesives to bond together two surfaces. The structural adhesives can be used, for example, to replace or augment conventional joining means such as welds or mechanical fasteners in bonding various surfaces together.

The curable compositions are often in the form of a two-part composition. The epoxy resin is typically separated from the curing agent prior to use of the curable composition. That is, the epoxy resin is typically in a first part and the curing agent is typically in a second part of the curable composition. The first part can include other components that do not react with the epoxy resin or that react with only a portion of the epoxy resin. Likewise, the second part can include other components that do not react with the curing agent or that react with only a portion of the curing agent. Various optional components such as a toughening agent, oil displacing agent, or filler can be included in the first part, in the second part, or in both the first part and the second part. When the first part and the second part are mixed together, the various components react to form the cured composition.

The epoxy resin that is included in the first part contains at least one epoxy functional group (i.e., oxirane group) per molecule. As used herein, the term oxirane group refers to the following divalent group.

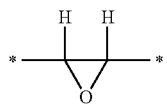

The asterisks denote a site of attachment of the oxirane group to another group. If the oxirane group is at the terminal position of the epoxy resin, the oxirane group is typically bonded to a hydrogen atom.

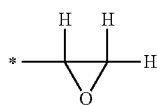

The epoxy resin has at least one oxirane group per molecule and often has at least two oxirane groups per molecule. For example, the epoxy resin can have 1 to 10, 2 to 10, 1 to 6, 2 to 6, 1 to 4, or 2 to 4 oxirane groups per molecule. The oxirane group is often part of a glycidyl group.

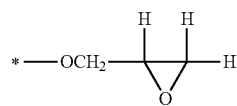

Epoxy resins can be a single material or a mixture of materials selected to provide the desired viscosity characteristics before curing and to provide the desired mechanical properties after curing. If the epoxy resin is a mixture of materials, at least one of the epoxy resins in the mixture is typically selected to have at least two oxirane groups per molecule. For example, a first epoxy resin in the mixture can have two to four oxirane groups and a second epoxy resin in the mixture can have one to six oxirane groups. In some of these examples, the first epoxy resin is a glycidyl ether with two to four glycidyl groups and the second epoxy resin is a glycidyl ether with one to six glycidyl groups.

The portion of the epoxy resin molecule that is not an oxirane group (i.e., the epoxy resin molecule minus the oxirane groups) can be aromatic, aliphatic, or a combination thereof and can be linear, branched, cyclic, or a combination thereof. The aromatic and aliphatic portions of the epoxy resin can include heteroatoms or other groups that are not reactive with the oxirane groups. That is, the epoxy resin can include halo groups, oxy groups such as in ether linkage groups, thio groups such as in thio ether linkage groups, carbonyl groups, carbonyloxy groups, carbonylimino groups, phosphono groups, sulfono groups, nitro groups, nitrile groups, and the like. The epoxy resin can also be a silicone-based material such as a polyorganosiloxane-based material.

Although the epoxy resin can have any suitable molecular weight, the weight average molecular weight is usually at least 100 grams/mole, at least 150 grams/mole, at least 175 grams/mole, at least 200 grams/mole, at least 250 grams/mole, or at least 300 grams/mole. The weight average molecular weight can be up to 50,000 gram/mole or even higher for polymeric epoxy resins. The weight average molecular weight is often up to 40,000 grams/mole, up to 20,000 grams/mole, up to 10,000 grams/mole, up to 5,000 grams/mole, up to 3,000 grams/mole, or up to 1,000 grams/mole. For example, the weight average molecular weight can be in the range of 100 to 50,000 grams/mole, in the range of 100 to 20,000 grams/mole, in the range of 100 to 10,000 grams/mole, in the range of 100 to 5,000 grams/mole, in the range of 200 to 5,000 grams/mole, in the range of 100 to 2,000 grams/mole, in the range of 200 to 2,000 gram/mole, in the range of 100 to 1,000 grams/mole, or in the range of 200 to 1,000 grams/mole.

Suitable epoxy resins are typically a liquid at room temperature (e.g., about 20° C. to about 25° C.). However, epoxy resins that can be dissolved in a suitable solvent also can be used. In many embodiments, the epoxy resin is a glycidyl ether. Examples of glycidyl ethers can be of Formula (XI).

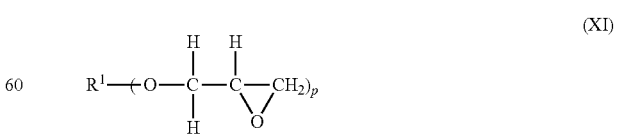

In Formula (XI), group $R^1$ is a p-valent group that is aromatic, aliphatic, or a combination thereof. Group $R^1$ can be linear, branched, cyclic, or a combination thereof. Group $R^1$ can optionally include halo groups, oxy groups, thio groups, carbonyl groups, carbonyloxy groups, carbonylimino groups, phosphono groups, sulfono groups, nitro groups, nitrile groups, and the like. Although the variable p can be any suitable integer greater than or equal to 1, p is often an integer in the range of 1 to 10, in the range 2 to 10, in the range of 2 to 6, or in the range of 2 to 4.

In some example epoxy resins of Formula (XI), the variable p is equal to 2 (i.e., the epoxy resin is a diglycidyl ether) and $R^1$ includes an alkylene (i.e., an alkylene is a divalent radical of an alkane and can be referred to as an alkane-diyl), heteroalkylene (i.e., a heteroalkylene is a divalent radical of a heteroalkane and can be referred to as a heteroalkane-diyl), arylene (i.e., a divalent radical of a arene compound, which is an aromatic hydrocarbon), heteroarylene (i.e., a divalent radical of a heteroarene compound, which is an aromatic compound having at least one heteroatom selected from oxygen, sulfur, or nitrogen), or combination thereof. Suitable alkylene groups often have 1 to 20 carbon atoms, 1 to 12 carbon atoms, 1 to 8 carbon atoms, or 1 to 4 carbon atoms. Suitable heteroalkylene groups often have 2 to 50 carbon atoms, 2 to 40 carbon atoms, 2 to 30 carbon atoms, 2 to 20 carbon atoms, 2 to 10 carbon atoms, or 2 to 6 carbon atoms with 1 to 10 heteroatoms, 1 to 6 heteroatoms, or 1 to 4 heteroatoms. The heteroatoms in the heteroalkylene can be selected from oxy, thio, or —NH— groups but are often oxy groups. Suitable arylene groups often have 6 to 18 carbon atoms or 6 to 12 carbon atoms. For example, the arylene can be phenylene or biphenylene. Suitable heteroarylene groups often have 3 to 18 carbon atoms or 3 to 12 carbon atoms. Group $R^1$ can further optionally include halo groups, oxy groups, thio groups, carbonyl groups, carbonyloxy groups, carbonylimino groups, phosphono groups, sulfono groups, nitro groups, nitrile groups, and the like. The variable p is usually an integer in the range of 2 to 4.

Some epoxy resins of Formula (XI) are diglycidyl ethers where $R^1$ includes (a) an arylene group or (b) an arylene group in combination with an alkylene, heteroalkylene, or both. Group $R^1$ can further include optional groups such as halo groups, oxy groups, thio groups, carbonyl groups, carbonyloxy groups, carbonylimino groups, phosphono groups, sulfono groups, nitro groups, nitrile groups, and the like. These epoxy resins can be prepared, for example, by reacting an aromatic compound having at least two hydroxyl groups with an excess of epichlorohydrin. Examples of useful aromatic compounds having at least two hydroxyl groups include, but are not limited to, resorcinol, catechol, hydroquinone, p,p'-dihydroxydibenzyl, p,p'-dihydroxyphenylsulfone, p,p'-dihydroxybenzophenone, 2,2'-dihydroxyphenyl sulfone, and p,p'-dihydroxybenzophenone. Still other examples include the 2,2', 2,3', 2,4', 3,3', 3,4', and 4,4' isomers of dihydroxydiphenylmethane, dihydroxydiphenyldimethylmethane, dihydroxydiphenylethylmethylmethane, dihydroxydiphenylmethylpropylmethane, dihydroxydiphenylethylphenylmethane, dihydroxydiphenylpropylenphenylmethane, dihydroxydiphenylbutylphenylmethane, dihydroxydiphenyltolylethane, dihydroxydiphenyltolylmethylmethane, dihydroxydiphenyldicyclohexylmethane, and dihydroxydiphenylcyclohexane.

Some commercially available diglycidyl ether epoxy resins of Formula (XI) are derived from bisphenol A (i.e., bisphenol A is 4,4'-(propane-2,2-diyl)diphenol). Examples include, but are not limited to, those available under the trade designation EPON (e.g., EPON 828, EPON 872, and EPON 1001) from Hexion Specialty Chemicals, Inc. (Houston, Tex., USA), those available under the trade designation D.E.R. (e.g., D.E.R. 331, D.E.R. 332, and D.E.R. 336) from Dow Chemical Co. (Midland, Mich., USA), and those available under the trade designation EPICLON (e.g., EPICLON 850) from Dainippon Ink and Chemicals, Inc. (Chiba, Japan). Other commercially available diglycidyl ether epoxy resins are derived from bisphenol F (i.e., bisphenol F is 2,2'-dihydroxydiphenylmethane). Examples include, but are not limited to, those available under the trade designation D.E.R. (e.g., D.E.R. 334) from Dow Chemical Co. and those available under the trade designation EPICLON (e.g., EPICLON 830) from Dainippon Ink and Chemicals, Inc.

Other epoxy resins of Formula (XI) are diglycidyl ethers of a poly(alkylene oxide)diol. These epoxy resins also can be referred to as diglycidyl ethers of a poly(alkylene glycol)diol. The variable p is equal to 2 and $R^1$ is a heteroalkylene having oxygen heteroatoms. The poly(alkylene glycol) portion can be a copolymer or homopolymer and often include alkylene units having 1 to 4 carbon atoms. Examples include, but are not limited to, diglycidyl ethers of poly(ethylene oxide)diol, diglycidyl ethers of poly(propylene oxide)diol, and diglycidyl ethers of poly(tetramethylene oxide)diol. Epoxy resins of this type are commercially available from Polysciences, Inc. (Warrington, Pa., USA) such as those derived from a poly(ethylene oxide)diol or from a poly(propylene oxide)diol having a weight average molecular weight of about 400 grams/mole, about 600 grams/mole, or about 1000 gram/mole.

Still other epoxy resins of Formula (XI) are diglycidyl ethers of an alkane diol (R' is an alkylene and the variable p is equal to 2). Examples include a diglycidyl ether of cylcohexane dimethanol, diglycidyl ether of 1,4-butanediol, and diglycidyl ethers of the cycloaliphatic diol formed from a hydrogenated bisphenol A such as those commercially available under the trade designation EPONEX 1510 from Hexion Specialty Chemicals, Inc. (Columbus, Ohio, USA).

Yet other epoxy resins include silicone resins with at least two glycidyl groups and flame retardant epoxy resins with at least two glycidyl groups (e.g., a brominated bisphenol-type epoxy resin having with at least two glycidyl groups such as that commercially available from Dow Chemical Co. (Midland, Mich., USA) under the trade designation D.E.R. 580).

Plant-based epoxy resins can be used. Suitable plant-based epoxy resins are commercially available, for example, from Nagase Chem Tex (Tokyo, Japan) under the trade designations EX-313, EX-512, and EX-521. Further, bisanhydrohexitol-based epoxy resins such as isosorbide diglycidyl ethers can be synthesized as described in U.S. Pat. No. 3,272,845 (Zech et al.). Sorbitol polyglycidyl polyether is commercially available from CVC Thermoset Specialties (Moorestown, N.J., USA) under the trade designation ERISYS GE-60. The combination of a plant-based epoxy resins with the plant-based curing agent of Formula (I) may be desirable for some applications. Plant-based epoxy resins derived from carbohydrates tend to be hydrophilic and are readily compatible with the hydrophilic compounds of Formula (I).

The epoxy resin is often a mixture of materials. For example, the epoxy resins can be selected to be a mixture that provides the desired viscosity or flow characteristics prior to curing. The mixture can include at least one first epoxy resin that is referred to as a reactive diluent that has a lower viscosity and at least one second epoxy resin that has a higher viscosity. The reactive diluent tends to lower the viscosity of the epoxy resin mixture and often has either a branched backbone that is saturated or a cyclic backbone that is saturated or unsaturated. Examples include, but are not limited to, the diglycidyl ether of resorcinol, the diglycidyl ether of cyclohexane dimethanol, the diglycidyl ether of neopentyl glycol, and the triglycidyl ether of trimethylolpropane. Diglycidyl ethers of cyclohexane dimethanol are commercially available under the trade designation HELOXY MODIFIER 107 from Hexion Specialty Chemicals (Columbus, Ohio, USA) and under the trade designation EPODIL 757 from Air Products and Chemical Inc. (Allentonwn, Pa., USA). Other reactive diluents have only one functional group (i.e., oxirane group) such as various monoglycidyl ethers. Some example monoglycidyl ethers include, but are not limited to, alkyl glycidyl ethers with an alkyl group having 1 to 20 carbon atoms, 1 to 12 carbon atoms, 1 to 8 carbon atoms, or 1 to 4 carbon atoms. Some example monoglycidyl ethers are commercially available under the trade designation EPODIL from Air Products and Chemical, Inc. (Allentown, Pa., USA) such as EPODIL 746 (2-ethylhexyl glycidyl ether), EPODIL 747 (aliphatic glycidyl ether), and EPODIL 748 (aliphatic glycidyl ether).

The epoxy resin often includes one or more glycidyl ethers. Epoxy resins with glycidyl ether groups tend to be more reactive than other types of epoxy resins. In some embodiments, such as those in which a plurality of different kinds of curing agents are used (e.g., a first curing agent that is a compound of Formula (I) and a second curing agent) other less reactive epoxy resins can be used. These less reactive epoxy resins, for example, can be epoxy alkanes, epoxy fluorinated alkanes, and epoxy esters such as glycidyl esters.

Suitable glycidyl esters are of Formula (XII).

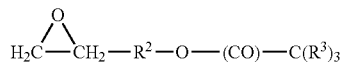

(XII)

In Formula (XII), group $R^2$ is an alkylene having 1 to 18 carbon atoms, 1 to 12 carbon atoms, 1 to 10 carbon atoms, 1 to 8 carbon atoms, 1 to 6 carbon atoms, or 1 to 4 carbon atoms. In some example compounds of Formula (XII), group $R^2$ is methylene. Each group $R^3$ is independently a linear or branched alkyl have 1 to 12 carbon atoms, 1 to 10 carbon atoms, 1 to 8 carbon atoms, 1 to 6 carbon atoms, or 1 to 4 carbon atoms. One example compound of Formula (XI) is commercially available under the trade designation CARDURA N10 from Hexion Specialty Chemicals (Columbus, Ohio, USA). This material is a glycidyl ester of a highly branched tertiary carboxylic acid (neodecanoic acid) that has 10 carbon atoms.

Other suitable epoxy resins can be selected from an epoxy alkane or epoxy fluorinated alkane of Formula (XIII).

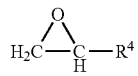

(XIII)

In Formula (XIII), group $R^4$ is an alkyl or fluorinated alkyl. The alkyl or fluorinated alkyl group can be linear, branched, cyclic, or a combination thereof. The alkyl or fluorinated alkyl group often has at least 3 carbon atoms such as 3 to 20 carbon atoms, 4 to 20 carbon atoms, 4 to 18 carbon atoms, 4 to 12 carbon atoms, or 4 to 8 carbon atoms. Example compounds of Formula (XII) include, but are not limited to, 1H,1H,2H-perfluoro(1,2-epoxy)hexane, 3,3-dimethyl-1,2-epoxybutane, 1,2-epoxyoctane, 1,2-epoxyhexane, 1,2-epoxybutane, 1,2-epoxydodecane, 1,2-epoxydecane, and 1,2-epoxycyclopentane.

Still other suitable epoxy resins are cyclic terpene oxides. Examples include, but are not limited to, limonene oxide, limonene dioxide, and alpha-pinene oxide.

The curable composition typically includes at least 20 weight percent epoxy resin based on a combined weight of the epoxy resin and curing agent. For example, the curable composition can include at least 25 weight percent, at least 30 weight percent, at least 40 weight percent, or at least 50 weight percent epoxy resin. The curable composition often includes up to 90 weight percent epoxy resin. For example, the curable composition can include up 80 weight percent, up to 75 weight percent, up to 70 weight percent, up to 65 weight percent, or up to 60 weight percent epoxy resin. Some example curable compositions contain 20 to 90 weight percent, 20 to 80 weight percent, 20 to 70 weight percent, 30 to 90 weight percent, 30 to 80 weight percent, 30 to 70 weight percent, 30 to 60 weight percent, 40 to 90 weight percent, 40 to 80 weight percent, 40 to 70 weight percent, 50 to 90 weight percent, 50 to 80 weight percent, or 50 to 70 weight percent epoxy resin.

The epoxy resin is cured by reacting with a curing agent that is typically in a second part of the curable composition. The curing agent includes the mercaptan compound of Formula (I). The epoxy resin is typically separated from the curing agent during storage or prior to using the curable composition. When the first part and the second part of the curable composition are mixed together, a mercapto group in the compound of Formula (I) reacts with an oxirane group in the epoxy resin. This reaction opens up the oxirane groups and links the curing agent to the epoxy resin.

A range of concentrations can be used for the curing agent depending on the curing temperature. In many embodiments, if low curing temperatures are used, more of the mercaptan compound of Formula (I) is included in the curable composition. If the curing reaction occurs at room temperature, the ratio of mercaptan hydrogen equivalent weight to epoxy equivalent weight in the curable composition is often at least 0.5:1, at least 0.8:1, or at least 1:1. The ratio can up be to 2:1, up to 1.5:1, up to 1.2:1, or up to 1.1:1. For example, the ratio can be in the range of 0.5:1 to 2:1, in the range of 0.5:1 to 1.5:1, in the range of 0.8:1 to 2:1, in the range of 0.8:1 to 1.5:1, in the range of 0.8:1 to 1.2:1, in the range of 0.9:1 to 1.1:1, or about 1:1.

Alternatively, if higher curing temperatures are used such as at least 80° C., less of the mercaptan compound of Formula (I) can be included in the curable composition. The amount of the curing agent in the curable composition is often present in a molar amount to react with only a portion of the epoxy resin. For example, the ratio of mercaptan hydrogen equivalent weight to epoxy equivalent weight is often less than 1:1 such in the range of 0.2:1 to 0.8:1, in the range of 0.2:1 to 0.6:1, or in the range of 0.3:1 to 0.5:1. Any epoxy resin that is not reacted with the curing agent tends to undergo homopolymerization at elevated temperatures.

The curable composition typically includes at least 20 weight percent first curing agent based on a combined weight of the epoxy resin and the first curing agent. For example, the curable composition can include at least 25 weight percent, at least 30 weight percent, at least 40 weight percent, or at least 50 weight percent first curing agent. The curable composition often includes up to 90 weight percent first curing agent. For example, the curable composition can include up 80 weight percent, up to 75 weight percent, up to 70 weight percent, up to 65 weight percent, or up to 60 weight percent first curing agent. Some example curable compositions contain 20 to 90 weight percent, 20 to 80 weight percent, 20 to 70 weight percent, 30 to 90 weight percent, 30 to 80 weight percent, 30 to 70 weight percent, 30 to 60 weight percent, 40 to 90 weight percent, 40 to 80 weight percent, 40 to 70 weight percent, 50 to 90 weight percent, 50 to 80 weight percent, or 50 to 70 weight percent first curing agent.

Some curable compositions contain 20 to 80 weight percent epoxy resin and 20 to 80 weight percent first curing agent based on a combined weight of the epoxy resin and the first curing agent. For example, the curable composition can include 30 to 70 weight percent epoxy resin and 30 to 70 weight percent first curing agent or 40 to 60 weight percent epoxy resin and 40 to 60 weight percent first curing agent.

In some embodiments, a second curing agent is combined with the first curing agent of Formula (I). The second curing agent has at least one group that is reactive with the epoxy resin. The second curing agent is often (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

The second curing agent can be combined with the first curing agent for a variety of reasons. For example, the second curing agent can be added to tailor the flexibility of the cured compositions. Different second curing agents can modulate the flexibility to a different extent. The flexibility can be characterized by measuring the overlap shear strength as described below. As the overlap shear strength increases, the cured composition tends to become more rigid. Similarly, as the overlap shear strength decreases, the cured composition tends to become more flexible.

Further, the addition of the second curing agent can result in an acid-base neutralization reaction. More specifically, the second curing agent can be basic and react with the acidic first curing agent of Formula (I). This type of reaction tends to occur particularly with the mercaptan compounds of Formula (I) where Y is a carbonyl group. This neutralization reaction can be exothermic. The resulting heat can be used advantageously to cure epoxy resins that are typically less reactive than epoxy resins that contain one or more glycidyl ether groups. For example, the heat can be used to cure epoxy alkanes and epoxy esters.

Some suitable second curing agents are amine compounds having at least one primary amino group or at least one secondary amino group. That is, the second curing agent has at least one group of formula —NR$^5$H where R$^5$ is selected from hydrogen, alkyl, aryl, heteroaryl, alkylaryl, or alkylheteroaryl. Suitable alkyl groups often have 1 to 12 carbon atoms, 1 to 8 carbon atoms, 1 to 6 carbon atoms, or 1 to 4 carbon atoms. The alkyl group can be cyclic, branched, linear, or a combination thereof. Suitable aryl groups usually have 6 to 12 carbon atom such as a phenyl or biphenyl group. Suitable alkylaryl groups can be either an alkyl substituted with an aryl or an aryl substituted with an alkyl. The same aryl and alkyl groups discussed above can be used in the alkylaryl groups. Suitable heteroaryl groups are aromatic groups having a heteroatom such as oxygen, nitrogen, or sulfur. The heteroaryl often has up to 10 carbon atoms and up to 4 heteroatoms, up to 6 carbon atoms and up to 3 heteroatoms, or up to 4 carbon atoms and up to 2 heteroatoms. Suitable alkylheteroaryl groups can be either an alkyl substituted with a heteroaryl or a heteroaryl substituted with an alkyl. The same heteroaryl and alkyl groups discussed above can be used in the alkylheteroaryl groups. When the second curing agent reacts with the epoxy resin, the oxirane group is opened and a covalent bond is formed linking the compound of amine compound to the epoxy resin. The reaction results in the formation of divalent groups of formula —OCH$_2$—CH$_2$—NR$^5$— where R$^5$ is equal to hydrogen, alkyl, aryl, heteroaryl, alkylaryl, or alkylheteroaryl. The portion of the amine compound second curing agent that is not an amino group can be any suitable aromatic group, aliphatic group, or combination thereof.

Some of the amine compounds useful as the curing agent are plant-based amines such as those having a single amino group of formula —NR$^5$H. Examples include, but are not limited to, dehydroabietylamine (DHAA), 2-aminomethylfuran (FA), and difurlyamines such as methylenebisfurylamine, ethylidenebisfurylamine, and 2-propylidenebisfurylamine. The difurylamines can be synthesized as described by Cawse et al., *Makromol. Chem.*, 185, pp. 697-707 (1984) and U.S. Pat. No. 5,292,903 (Conner et al.). The use of these plant-based amines in combination with the bio-based epoxy compounds of Formula (I) can be used to provide renewable curable compositions.

Some amine compound second curing agents are of Formula (XIII). In some of these compounds, there are at least two primary amino groups, at least two secondary amino groups, or at least one primary amino group and at least one secondary amino group.

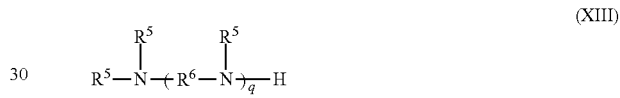

(XIII)

Each R$^5$ group is independently hydrogen, alkyl, aryl, heteroaryl, alkylaryl, or alkylheteroaryl as described above. Each R$^6$ is independently an alkylene, heteroalkylene, or combination thereof. Suitable alkylene groups often have 1 to 18 carbon atoms, 1 to 12 carbon atoms, 1 to 8 carbon atoms, 1 to 6 carbon atoms, or 1 to 4 carbon atoms. Suitable heteroalkylene groups have at least one oxy, thio, or —NH— group positioned between two alkylene groups. Suitable heteroalkylene groups often have 2 to 50 carbon atoms, 2 to 40 carbon atoms, 2 to 30 carbon atoms, 2 to 20 carbon atoms, or 2 to 10 carbon atoms and with up to 20 heteroatoms, up to 16 heteroatoms, up to 12 heteroatoms, or up to 10 heteroatoms. The heteroatoms are often oxy groups. The variable q is an integer equal to at least one and can be up to 10 or higher, up to 5, up to 4, or up to 3.

Some amine curing agents of Formula (XIII) can have an R$^6$ group selected from an alkylene group. Examples include, but are not limited to, ethylene diamine, diethylene diamine, diethylene triamine, triethylene tetramine, propylene diamine, tetraethylene pentamine, hexaethylene heptamine, hexamethylene diamine, 2-methyl-1,5-pentamethylene diamine, 1-amino-3-aminomethyl-3,3,5-trimethylcyclohexane (also called isophorene diamine), N',N'-1,5-bisfuranyl-2-methylmethylene-pentane-1,5-diamine (TEKA), and the like. Other amine curing agents can have an R$^6$ group selected from a heteroalkylene group such as a heteroalkylene having oxygen heteroatoms. For example, the curing agent can be a compound such as aminoethylpiperazine, 4,7,10-trioxatridecane-1,13-diamine (TTD) available from TCI America (Portland, Oreg., US), or a poly(alkylene oxide)diamine (also called a polyether diamine) such as a poly(ethylene oxide) diamine, poly(propylene oxide)diamine, or a copolymer thereof. Commercially available polyether diamines are commercially available under the trade designation JEFFAMINE form Huntsman Corporation (The Woodlands, Tex., USA).

Still other amine curing agents can be formed by reacting a polyamine (i.e., a polyamine refers to an amine with at least two amino groups selected from primary amino groups and secondary amino groups) with another reactant to form an amine-containing adduct having at least two amino groups. For example, a polyamine can be reacted with an epoxy resin to form an adduct having at least two amino groups. If a polymeric diamine is reacted with a dicarboxylic acid in a molar ratio of diamine to dicarboxylic acid that is greater than or equal to 2:1, a polyamidoamine having two amino groups can be formed. Such a polyamidoamine can be prepared as described, for example, in U.S. Pat. No. 5,629,380 (Baldwin et al.). In another example, if a polymeric diamine is reacted with an epoxy resin having two glycidyl groups in a molar ratio of diamine to epoxy resin greater than or equal to 2:1, an amine-containing adduct having two amino groups can be formed. A molar excess of the polymeric diamine is often used so that the curing agent includes both the amine-containing adduct plus free (non-reacted) polymeric diamine. For example, the molar ratio of diamine to epoxy resin with two glycidyl groups can be greater than 2.5:1, greater than 3:1, greater than 3.5:1, or greater than 4:1. Even when epoxy resin is used to form the amine-containing adduct in the second part of the curable composition, additional epoxy resin is present in the first part of the curable composition.

Other second curing agents can be imidazoles, imidazolines, or salts thereof. Examples include, but are not limited to, 2-methylimidazole, 2-hydroxypropylimidazole, 2-heptadecylimidazole, 2-ethyl-4-methylimidazole, 1-benzyl-2-methylimidazole, and the like. Some example imidazoles are commercially available under the trade designation CUREZOL and IMICURE from Air Products and Chemicals Inc. (Allentown, Pa., USA) and EPICURE P-101 from Momentive Specialty Chemicals (Houston, Tex., USA).

Still other second curing agents are phenols substituted with at least one group selected from a tertiary amino, tertiary alkyl, secondary alkyl, nitro, halo, hydroxyl, or combination thereof. Example phenols substituted with tertiary amino groups can be of Formula (XIV).

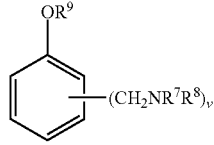

(XIV)

In Formula (XIV), each group $R^7$ and $R^7$ is independently an alkyl. The variable v is an integer equal to 2 or 3. Group $R^9$ is hydrogen or alkyl. Suitable alkyl groups for $R^7$, $R^8$, and $R^9$ often have 1 to 12 carbon atoms, 1 to 8 carbon atoms, 1 to 6 carbon atoms, or 1 to 4 carbon atoms. One example secondary curative of Formula (XIV) is tris-2,4,6-(dimethylaminomethyl)phenol that is commercially available under the trade designation ANCAMINE K54 from Air Products Chemicals, Inc. (Allentown, Pa., USA). Other example phenols not of Formula (VII) include, but are not limited to, 4-tert-butylphenol, nonylphenol, 2-nitrophenol, 4-nitrophenol, 2-chlorophenol, 4-chlorophenol, and catechol.

Bisphenol second curing agents include, for example, bisphenol A (i.e., 4,4'-(propane-2,2-diyOdiphenol), bisphenol F (i.e., bis(4-hydroxyphenyl)methane), and 2,2'-bisphenol. Suitable anhydride second curing agents include benzophenone tetracarboxylic acid anhydride, succinic anhydride, maleic anhydride, phthalic anhydride, and the like. Suitable carboxylic acid second curing agents include adipic acid, sebacic acid, terephthalic acid, isophthalic acid, salicylic acid, valeric acid, 2,4-dichlorobenzoic acid, and the like.

If the curing reaction of a curable composition with both a first curing agent and a second curing agent occurs at room temperature, the ratio of the combined hydrogen equivalent weight of the first curing agent plus the second curing agent to epoxy equivalent weight is often at least 0.5:1, at least 0.8:1, or at least 1:1. The ratio can up be to 2:1, up to 1.5:1, up to 1.2:1, or up to 1.1:1. For example, the ratio can be in the range of 0.5:1 to 2:1, in the range of 0.5:1 to 1.5:1, in the range of 0.8:1 to 2:1, in the range of 0.8:1 to 1.5:1, in the range of 0.8:1 to 1.2:1, in the range of 0.9:1 to 1.1:1, or about 1:1.

If the curing temperature occurs at elevated temperatures (e.g., at least 80° C., at least 100° C., at least 120° C., or at least 150° C.), however, a lower amount of the combined first curing agent and the second curing agent is often used. The amount of the curing agent in the curable composition is often present in a sufficient molar amount to react with only a portion of the epoxy resin. For example, the ratio of the combined hydrogen equivalent weight of the first curing agent plus the second curing agent to epoxy equivalent weight is often less than 1:1 such in the range of 0.2:1 to 0.8:1, in the range of 0.2:1 to 0.6:1, or in the range of 0.3:1 to 0.5:1. Any epoxy resin that is not reacted with either the first curing agent or the second curing agent tends to undergo homopolymerization at elevated temperatures.

Any molar ratio of first curing agent to the second curing agent can be used. In some embodiments, the ratio of the hydrogen equivalent weight of the second curing agent to the hydrogen equivalent weight of the first curing agent is often in the range of 0.1:1 to 10:1. For example, the ratio can be in the range of 0.2:1 to 8:1, in the range of 0.5:1 to 6:1, in the range of 1:1 to 6:1, or in the range of 2:1 to 6:1.

Some curable compositions contain 20 to 80 weight percent epoxy resin and 20 to 80 weight percent combined first curing agent and second curing agent. For example, the curable composition can include 30 to 70 weight percent epoxy resin and 30 to 70 weight percent combined first and second curing agent or 40 to 60 weight percent epoxy resin and 40 to 60 weight percent combined first and second curing agent. The amounts are based on a total weight of epoxy resin, first curing agent, and second curing agent.

The curable compositions optionally can include a toughening agent. Toughening agents are polymers other than the curable epoxy resins that are capable of enhancing the toughness of the cured composition. The toughening agents can be added to the first part of the curable composition with the epoxy resin, to the second part of the curable composition with the curing agent, or to both the first and second part of the curable composition. Typical toughening agents include core-shell polymers, butadiene-nitrile rubbers, acrylic polymers and copolymers, and the like.

Some toughening agents are core-shell polymers. A shell polymeric material is typically grafted to a core polymeric material. The core is usually an elastomeric material with a glass transition temperature less than 0° C. The shell is usually a polymeric material having a glass transition temperature greater than 25° C. The glass transition temperature can be determined using dynamic mechanical thermal analysis (DMTA) or a similar method.

The core of the core-shell polymeric toughening agents is often prepared from a butadiene polymer or copolymer, a styrene polymer or copolymer, an acrylonitrile polymer or copolymer, an acrylate polymer or copolymer, or combinations thereof. These polymers or copolymers can be crosslinked or not crosslinked. Some example cores are polymethylmethacrylates that are either crosslinked or not crosslinked. Other example cores are butadiene-styrene copolymers that are either crosslinked or not crosslinked.

The shell of the core-shell polymeric toughening agents are often formed from a styrene polymer or copolymer, a methacrylate polymer or copolymer, an acrylonitrile polymer or copolymer, or combinations thereof. The shell can be further functionalized with epoxy groups, acidic groups, or acetoacetoxy groups. Functionalization of the shell may be achieved, for example, by copolymerization with glycidylmethacrylate or acrylic acid or by reaction of a hydroxyl group with an alkyl acetoacetoxy such as tert-butyl acetoacetoxy. The addition of these functional groups can result in the shell being crosslinked into the polymeric matrix.

Suitable core-shell polymers often have an average particle size equal to at least 10 nanometers, at least 20 nanometers, at least 50 nanometers, at least 100 nanometers, at least 150 nanometers, or at least 200 nanometers. The average particle size can be up to 400 nanometers, up to 500 nanometers, up to 750 nanometers, or up to 1000 nanometers. The average particle size can be, for example, in the range of 10 to 1000 nanometers, in the range of 50 to 1000 nanometers, in the range of 100 to 750 nanometers, or in the range of 150 to 500 nanometers.

Example core-shell polymers and their preparation are described in U.S. Pat. No. 4,778,851 (Henton et al.). Commercially available core-shell polymers can be obtained, for example, under the trade designation PARALOID (e.g., PARALOID EXL 2600 and PARALOID EXL 2691) from Rohm & Haas Company (Philadelphia, Pa., USA) and under the trade designation KANE ACE (e.g., KANE ACE B564, KANE ACE MX120, KANE ACE MX257, and KANE ACE MX153) from Kaneka (Belgium).

Still other toughening agents can be prepared by reacting amino-terminated materials or carboxy-terminated materials with an epoxy resin to prepare an adduct that phase separates from the other components in the cured composition. Suitable amino-terminated materials that can be used to prepare such toughening agents include, but are not limited to, those commercially available under the trade designation DYNAMAR POLYETHERDIAMINE HC 1101 from 3M Corporation (Saint Paul, Minn., USA). This is a linear polymeric material. Suitable carboxy-terminated materials include carboxy-terminated butadiene acrylonitrile copolymers such as those commercially available from Emerald Chemical (Alfred, Me., USA).

Various optional accelerators such as various metal salts can be added. Useful metal salts include, for example, calcium ($Ca^{+2}$) salts, magnesium ($Mg^{+2}$) salts, bismuth ($Bi^{+3}$) salts, cerium ($Ce^{+3}$) salts, iron salts ($Fe^{+3}$), lead ($Pb^{+1}$) salts, copper ($Cu^{+2}$) salts, cobalt ($Co^{+2}$) salts, lanthanum ($La^{+3}$) salts, lithium ($Li^{+1}$) salts, indium ($In^{+3}$) salts, thallium ($Th^{+4}$) salts, beryllium ($Be^{+2}$) salts, barium ($Ba^{+2}$) salts, strontium ($Sr^{+2}$) salts, and zinc ($Zn^{+2}$) salts. In many embodiments, the accelerators are selected to be calcium salts, magnesium salts or lanthanum salts. Suitable anions of the metal salts include, but are not limited to, $NO_3^-$, $CF_3SO_3^-$, $ClO_4^-$, $BF_4^-$, $CH_3C_6H_4SO_3^-$, and $SbF_6^-$.

Other optional components such as fillers can be added to the curable compositions. The fillers can be added to the first part of the curable composition, to the second part of the curable composition, or to both the first part and the second part of the curable composition. Fillers are often added to promote adhesion, to improve corrosion resistance, to control the rheological properties, to reduce shrinkage during curing, to accelerate curing, to absorb contaminants, to improve heat resistance, or for a combination thereof. The fillers can be inorganic material, organic materials, or composite materials containing both inorganic and organic materials. The fillers can have any suitable size and shape. Some fillers are in the form of particles with spherical, elliptical, or platelet shapes. Other fillers are in the form of fibers.

Some fillers are inorganic fibers such as fiber glass (e.g., glass wool and glass filament), mineral wool (e.g., rock wool and slag wool), and refractory ceramic fibers. Some example inorganic fibers include a mixture of $SiO_2$, $Al_2O_3$, or a combination thereof. The inorganic fibers can further include CaO, MgO, $Na_2O$, $K_2O$, $Fe_2O_3$, $TiO_2$, other oxides, or mixtures thereof. Example inorganic fibers are commercially available under the trade designation COATFORCE (e.g., COATFORCE CF50 and COATFORCE CF10) from Lapinus Fibres BV (Roermond, The Netherlands). Other example inorganic fibers can be prepared from wollastonite (i.e., calcium silicate).

Other fillers are organic fibers such as aramid fibers and polyolefin fibers such as polyethylene fibers. These organic fibers can be untreated or treated to change their hydrophobic or hydrophilic character. For example, some organic fibers are specially treated to make them hydrophobic or to increase their hydrophobicity. The fibers can be fibrillated. Example polyolefin fibers include high-density polyethylene fibers such as those available under the trade designation SYLOTHIX (e.g., SYLOTHIX 52 and SYLOTHIX 53) from EP Minerals (Reno, Nev., USA), those available under the trade designation ABROTHIX (e.g., ARBOTHIX PE100) from EP Minerals, those available under the trade designation SHORT STUFF (e.g., SHORT STUFF ESS2F and SHORT STUFF ESS5F) from MiniFIBERS, Inc. (Johnson City, Tenn., USA), and those available under the trade designation INHANCE (e.g., INHANCE PEF) from Inhance/Fluoro-Seal, Limited (Houston, Tex., USA). Example aramid fibers are commercially available under the trade designation INHANCE (e.g., INHANCE KF) from Inhance/Fluoro-Seal, Ltd. (Houston, Tex., USA).

Other suitable fillers include silica-gels, calcium silicates, calcium nitrate, calcium phosphates, calcium molybdates, calcium carbonate, calcium hydroxide, fumed silica, clays such as bentonite, organo-clays, aluminium trihydrates, glass microspheres, hollow glass microspheres, polymeric microspheres, and hollow polymeric microspheres. The fillers can also be a pigment such as ferric oxide, brick dust, carbon black, titanium oxide, and the like. Any of these filler can be surface modified to make them more compatible with the curable or cured composition.

Example fillers include a mixture of synthetic amorphous silica and calcium hydroxide that is commercially available from W.R. Grace (Columbia, Md., USA) under the trade designation SHIELDEX (e.g., SHIELDEX AC5), a fumed silica treated with polydimethylsiloxane to prepare a hydrophobic surface that is available from Cabot GmbH (Hanau, Germany) under the trade designation CAB-O-SIL (e.g., CAB-O-SIL TS 720), a hydrophobic fumed silica available from Degussa (Düsseldorf, Germany) under the trade designation AEROSIL (e.g., AEROSIL VP-R-2935), glass beads class IV (250 to 300 micrometers) from CVP S.A. (France), and epoxysilane-functionalized (2 wt %) aluminium trihydrate available under the trade designation APYRAL 24ES2 from Nabaltec GmbH (Schwandorf, Germany).

The curable composition can include an optional adhesion promoter. Example adhesion promoters include, but are not limited to, various silane compounds. Some silane compounds that are suitable for adhesion promoters have amino groups or glycidyl groups that can react with one or more components in the curable composition. One such silane compound is a glycidoxypropyltrimethoxysilane that is commercially available under the trade designation SILANE Z6040 from Dow Corning (Midland, Mich., USA). Other example adhesive promoters include various chelating agents such as those described in U.S. Pat. No. 6,632,872 (Pellerite et al.) and various chelate-modified epoxy resins such as those available from Adeka Corporation (Tokyo, Japan) under the trade designation EP-49-10N and EP-49-20.

Solvents optionally can be included in the curable composition. The solvents are typically selected to be miscible with the curable composition. Solvents can be added to lower the viscosity of either the first part or the second part of the curable composition or can be added with one of the various components included in the curable composition. The amount of solvent is typically minimized and is often less than 15 weight percent based on a total weight of the curable composition. The solvent is often less than 12 weight percent, less than 10 weight percent, less than 8 weight percent, less than 6 weight percent, less than 4 weight percent, less than 2 weight percent, less than 1 weight percent, or less than 0.5 weight percent based on the total weight of the curable composition. Suitable organic solvents include those that are soluble in the curable composition and that can be removed during or after curing to form the cured composition. Example organic solvents include, but are not limited to, toluene, acetone, various alcohols, and xylene.

The curable composition typically is in the form of a first part and a second part. The first part typically includes the epoxy resins plus other components that do not react with the epoxy resin. The second part typically includes the curing agent plus any other components that do not react with the curing agent. The components in each part are typically selected to minimize reactivity within that part.

The various parts of the curable composition are mixed together to form the cured composition. These parts are typically mixed together immediately prior to use of the curable composition. The amount of each part included in the mixture can be selected to provide the desired molar ratio of oxirane groups to curing agent hydrogen atoms.

The curable composition can be cured at room temperature, can be cured at room temperature and then at an elevated temperature (e.g., at least 80° C., at least 100° C., at least 120° C., or at least 150° C.), or can be cured at an elevated temperature. In some embodiments, the curable composition can be cured at room temperature for at least 3 hours, at least 6 hours, at least 12 hours, at least 18 hours, at least 24 hours, at least 48 hours, or at least 72 hours. In other embodiments, the curable composition can be cured at room temperature for any suitable length of time and then further cured at an elevated temperature such as, for example, 180° C. for a time up to 10 minutes, up to 20 minutes, up to 30 minutes, up to 60 minutes, up to 120 minutes, or even longer than 120 minutes.

In another aspect, an article is provided that includes a first substrate and a cured composition positioned adjacent to the first substrate. The cured composition contains a reaction product of a curable composition that includes (a) an epoxy resin and (b) a first curing agent. The first curing agent is a mercaptan compound of Formula (I) as described above. Suitable substrates onto which the curable composition can be applied include metals (e.g., steel, iron, copper, aluminum, or alloys thereof), carbon fiber, glass fiber, glass, epoxy fiber composites, wood, polymeric materials, and mixtures thereof.

The cured compositions may be used as an adhesive such as a structural adhesive. The cured compositions may be used to supplement or completely eliminate a weld or mechanical fastener by applying the curable composition between two parts (i.e., between two surfaces of two substrates) to be joined and curing the adhesive to form a bonded joint. In some embodiments, at least one of the substrates is a metal. In other embodiments, both substrates are metal. Alternatively, the cured compositions can be used to provide a polymeric coating on a substrate.

When used as an adhesive, the cured composition can be augmented by welding or mechanical fastening. The welding can occur as spot welds, as continuous seam welds, or as any other welding technology that can cooperate with the adhesive composition to form a mechanically sound joint. In some embodiments, the structural adhesives are used in vehicle assembly, in architectural applications, or in various household and industrial appliances.

The curable composition can be applied as liquid, paste, spray, or solid that can be liquefied upon heating. The application can be as a continuous bead or as dots, stripes, diagonals or any other geometrical form that will result in the formation of a useful bond. In some embodiments, the curable composition is in a liquid or paste form.

In another aspect, a method of making a composite article is provided. The method includes applying a two-part curable composition to a substrate, and curing the two-part curable adhesive while in contact with the substrate to form a composite article. The resulting cured composition can function as a polymeric coating for the substrate.

In yet another aspect, a method of forming a bonded joint between substrates is provided. The method includes applying a two-part curable composition to a surface of at least one of two or more substrates, joining the substrates so that the two-part curable composition is positioned between the two or more substrates, and curing the curable composition to form a bonded joint between the two or more substrates.

Compared to some known petroleum-based dimercaptan compounds such as ethylene glycol dithioglycolate (EGDTG), the plant-based mercaptan compounds of Formula (I) and, most especially, the plant-based mercaptan esters compounds of Formula (II) tend to result in the formation of a cured composition having a higher overlap shear strength.

Various items are provided that are compounds, curable compositions, or articles.

Item 1 is a compound of Formula (I).

$$\text{HS-L-Y—O-Q-O—Y-L-SH} \tag{I}$$

In this formula, each Y is independently a single bond or a carbonyl group and each L is independently an alkylene or heteroalkylene. The group Q is a divalent group of Formula (I-1), Formula (I-2), or Formula (I-3).

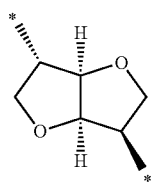

(I-1)

(I-2)

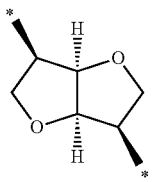

(I-3)

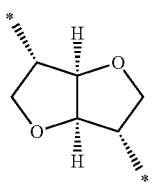

Item 2 is the compound of item 1, wherein the compound is a liquid at 25° C.

Item 3 is the compound of item 1, wherein the compound of Formula (I) is of Formula (II)

HS-L-(CO)—O-Q-O—(CO)-L-SH     (II)

Item 4 is the compound of item 3, wherein the compound of Formula (II) is

HS—CH$_2$—(CO)—O-Q-O—(CO)—CH$_2$—SH,

HS—CH(CH$_3$)—(CO)—O-Q-O—(CO)—CH(CH$_3$)—SH, or

HS—CH$_2$CH$_2$—(CO)—O-Q-O—(CO)—CH$_2$CH$_2$—SH.

Item 5 is the compound of item 1, wherein the compound of Formula (I) is of Formula (III)

HS-L-O-Q-O-L-SH     (III)

Item 6 is the compound of item 5, wherein the compound of Formula (III) is HS—CH$_2$CH$_2$CH$_2$—O-Q-O—CH$_2$CH$_2$CH$_2$—SH.

Item 7 is a curable composition comprising a) an epoxy resin and b) a first curing agent of Formula (I).

HS-L-Y—O-Q-O—Y-L-SH     (I)

In this formula, each Y is independently a single bond or a carbonyl group and each L is independently an alkylene or heteroalkylene. The group Q is a divalent group of Formula (I-1), Formula (I-2), or Formula (I-3).

(I-1)

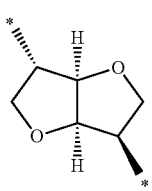

(I-2)

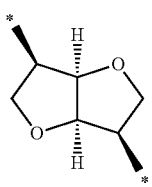

(I-3)

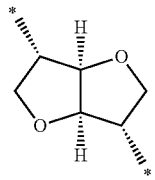

Item 8 is the curable composition of item 7, further comprising a second curing agent comprises (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

Item 9 is the curable composition of item 7, further comprising a second curing agent having a group of formula —NR$^5$H where R$^5$ is hydrogen, alkyl, aryl, heteroaryl, alkylaryl, or alkylheteroaryl.

Item 10 is the curable composition of any one of items 7 to 9, wherein the first curing agent of Formula (I) is of Formula (II).

HS-L-(CO)—O-Q-O—(CO)-L-SH     (II)

Item 11 is the curable composition of any one of items 7 to 9, wherein the first curing agent of Formula (I) is of Formula (III).

HS-L-O-Q-O-L-SH     (III)

Item 12 is the curable composition of any one of items 7 to 11, wherein the curable composition has a first part comprising the epoxy resin and a second part comprising the compound of Formula (I).

Item 13 is an article that includes a first substrate and a cured composition positioned adjacent to the first substrate. The cured composition comprises a reaction product of a curable composition comprising a) an epoxy resin and b) a first curing agent of Formula (I).

HS-L-Y—O-Q-O—Y-L-SH     (I)

In Formula (I), each Y is independently a single bond or a carbonyl group and each L is independently an alkylene or heteroalkylene. Group Q is a divalent group of Formula (I-1), Formula (I-2), or Formula (I-3).

(I-1)

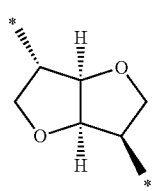

(I-2)

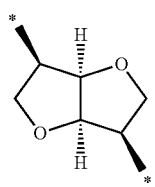

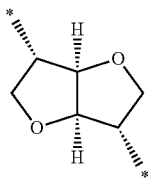
(I-3)

Item 14 is the article of item 13, wherein the first curing agent of Formula (I) is of Formula (II).

HS-L-(CO)—O-Q-O—(CO)-L-SH    (II)

Item 15 is the article of item 13, wherein the first curing agent of Formula (I) is of Formula (III).

HS-L-O-Q-O-L-SH    (III)

Item 16 is the article of any one of items 13 to 15, further comprising a second curing agent comprises (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

Item 17 is the article of any one of items 13 to 15, wherein the curable composition further comprises a second curing agent having a group of formula —$NR^5H$ where $R^5$ is hydrogen, alkyl, aryl, heteroaryl, alkylaryl, or alkylheteroaryl.

Item 18 is the article of any one of items 13 to 17, wherein the curable composition is a coating on the substrate.

Item 19 is the article of any one of items 13 to 17, wherein the article has two substrates and the curable composition is a structural adhesive bonding the two substrates together.

EXAMPLES

The particular materials and amounts thereof recited in these examples, as well as other conditions and details, should not be construed as being unduly limiting. These examples are merely for illustrative purposes and are not meant to be limiting on the scope of the appended claims.

Solvents and other reagents used can be obtained from Aldrich Chemical Company, Milwaukee, Wis. unless otherwise noted.

Materials Used

Allyl bromide was obtained from Alfar Aesar (Ward Hill, Mass., USA).

Technical grade tris-2,4,6-dimethylaminomethyl-phenol catalytic tertiary amine additive was obtained from Air Products and Chemicals, Inc. (Allentown, Pa., USA) under the trade designation ANCAMINE K54 (K54).

The compound 2-aminomethylfuran (FA) was obtained from Alfar Aesar (Ward Hill, Mass., USA).

The compound 2,2'azobis(2-methylbutyronitrile) is a free radical initiator that is commercially available under the trade designation VAZO 67 from DuPont (Wilmington, Del., USA).

Dehydroabietylamine (DHAA) is a rosin acid derivative that was obtained from TCI America (Portland, Oreg., USA).

Dipentene dimercaptan (DPDM) was obtained from Chevron Philips Chemical (The Woodlands, Tex., USA).

DTA is a multifunctional dimer diamine with an amine hydrogen equivalent weight of 137. It is commercially available from Croda, USA Inc. (Edison, N.J., USA).

Ethylene glycol dithioglycolate (EGDTG)

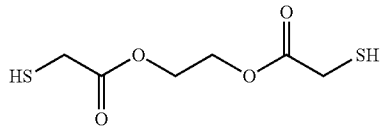 [SMILES: O=C(CS)OCCOC(=O)CS]

was obtained from Pfaltz & Bauer, Inc. (West Chester, Pa., USA).

Diglycidyl ether of Bisphenol A with an epoxy equivalent weight of 188 was obtained from Shell Chemical (Houston, Tex., USA) under the trade designation EPON 828 Resin.

Glycerol polyglycidyl ether with epoxy equivalent weight of 141 was obtained from Nagase ChemTex (Tokyo, Japan) under the trade designation EX-313.

Isosorbide diglycidyl ether (IDGE) was synthesized following the method described in U.S. Pat. No. 3,272,845 (Zech et al.).

Isosorbide was obtained from Roquette America Inc. (Geneva, Ill., USA).

Limonene dioxide (LDO), which is dipentene diepoxide,

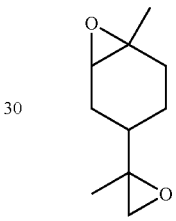

was obtained from Arkema Inc. (King of Prussia, Pa., USA).

Mercaptoacetic acid was obtained from Alfa Aesar (Ward Hill, Mass., USA).

The compounds 2-mercaptopropionic acid and 3-mercaptopropionnic acid were obtained from Alfa Aesar (Ward Hill, Mass., USA).

Methane sulfonic acid was obtained from Alfa Aesar (Ward Hill, Mass., USA).

The compound 2-methylpentamethylenediamine is commercially available under the trade designation DYTEK A from Invista (Wilmington, Del., USA).

CELITE is a trade designation of Fluka, Sigma-Aldrich Corp. (St. Louis, Mo., USA) for a diatomaceous earth filter aide.

Platinum (IV) oxide, $PtO_2$, was obtained from Alfa Aesar (Ward Hill, Pa., USA).

The compound N',N'-1,5-bisfuranyl-2-methylmethylenepentane-1,5-diamine (TEKA) with an amine hydrogen equivalent weight of 138.2 grams/equivalent was synthesized.

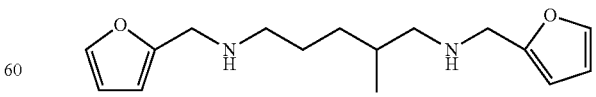

In a Parr pressure vessel (Parr Instrument Co., Moline, Ill., USA), platinum oxide (200 milligrams) was added to ethanol (200 mL). The vessel was evacuated and filled with hydrogen three times. The vessel was refilled to 60 pounds per square inch (psi) (0.41 Mpa) with hydrogen and then rocked for 1 hour to pre-reduce the catalyst. The vessel was then evacuated and refilled with nitrogen three times. Furfural (35.00 grams, 0.36 moles) and DYTEK A (21.23 grams, 0.18 moles) were added. The vessel was evacuated and refilled with hydrogen three times. The vessel was then filled with hydrogen to 60 (psi) (0.41 Mpa) and rocked at room temperature for 1 week. The vessel was evacuated and refilled with nitrogen three times and then 10 weight percent platinum on carbon (100 milligrams) was added. The vessel was evacuated and refilled three times with hydrogen. The vessel was then filled with hydrogen to 60 psi and rocked for 3 days. The vessel was evacuated and refilled with nitrogen three times. The mixture was then filtered through CELITE and concentrated under vacuum overnight to yield the desired product as a brown oil (50.72 grams).

Pentaerythritol tetrakis(3-mercaptopropionate) (PETMP) was obtained from Sigma Aldrich (Milwaukee, Wis., USA).

Polyglycerol polyglycidyl ether with epoxy equivalent weight of 168 was obtained from Nagase ChemTex (Tokyo, Japan) under the trade designation EX-512.

Polyglycerol polyglycidyl ether with epoxy equivalent weight of 183 was obtained from Nagase ChemTex (Tokyo, Japan) under the trade designation EX-521.

Sorbitol polyglycidyl polyether with an epoxy equivalent weight of 195 was obtained from CVC Thermoset Specialties (Moorestown, N.J., USA) under the trade designation ERISYS GE-60.

Thio-acetic acid was obtained from Alfar Aesar (Ward Hill, Mass., USA).

Generation of Overlap Shear Bonds

Overlap shear bond test specimens were made using cleaned, cold-rolled steel panels. The panels were cleaned three times with toluene followed by another three times with acetone. The panels were obtained from Q-Lab Corporation (Cleveland, Ohio, USA) and were iron phosphate (B-1000) steel panels (type "RS" steel) having square corners and measuring 4 inch×1 inch×0.063 inch (10.2 cm×2.54 cm×0.16 cm). The test specimens were generated as described in ASTM Specification D 1002-05. An adhesive strip that was approximately 0.5 inches (1.27 cm) wide and 0.010 inch (0.254 mm) thick was applied to one edge of each of two steel panels using a wooden scraper. Glass beads (approximately 250 micrometers in diameter) were sprinkled throughout the adhesive and served as spacers. The bond was closed and clamped using a 1 inch (2.54 cm) binder clip to apply pressure to provide for adhesive spreading. After the adhesive had been allowed to cure (as described in the examples), the bonds were tested to failure at room temperature on a Sintech Tensile Testing machine obtained from MTS (Eden Prairie, Minn., USA) using a crosshead displacement rate of 0.1 inch/minute (2.54 mm/minute). The failure load was recorded. The lap width was measured with a Vernier caliper. The quoted lap shear strengths were calculated as failure load divided by measured bond area. The average and standard deviation were calculated from the results of at least three tests unless otherwise noted.

Adhesive Preparation

All adhesive samples were prepared by mixing the epoxy resin with the curing agent (mercapto-containing compounds or mixtures of mercapto-containing compounds and amino-containing compounds) thoroughly in a plastic cup using a DAC 400 high speed mixer, which can be obtained from FlackTek, Inc. (Landrum, S.C., USA). Unless otherwise stated, overlap shear bond test specimens were prepared from the adhesives as described above. The samples were cured at room temperature for a minimum of 16 hours followed by another one hour at 150° C. unless otherwise noted.

Cure Temperature Determination

Cure temperature was determined by differential scanning calorimetry using a Model DSC Q200 instrument available from TA Instruments (New Castle, Del., USA). A sample of approximately 10 milligrams was placed into hermetic aluminum DSC pans and crimped to seal. The sample was heated at a rate of 3° C./minute from 30° C. to 350° C. under nitrogen flow (50 mL/minute). The temperature at the peak maximum of the resulting heat flow versus temperature curve was noted as the cure temperature.

Example 1

Isosorbide bis-thioglycolate (ISTG)

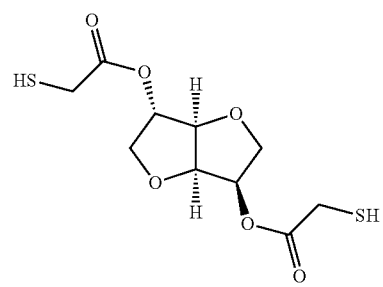 [SMILES: O=C(CS)O[C@H]1CO[C@H]2[C@@H]1OC[C@H]2OC(=O)CS]

A mixture of isosorbide (60.00 grams, 0.41 moles), mercaptoacetic acid (83.21 grams, 0.90 moles), toluene (300 mL), and methane sulfonic acid (1.00 grams, 10 mmoles) was heated to reflux. Water was separated from the toluene/water azeotrope using a Dean Stark distillation trap. After four hours at reflux, a total of 15 mL of water was collected in the trap. The reaction mixture was cooled and washed with saturated aqueous sodium bicarbonate (2×200 mL) and brine (100 mL). The solution was dried over magnesium sulfate and then concentrated under reduced pressure. The product was a colorless oil. (Yield: 106.10 grams).

Example 2

Isosorbide bis-(2-mercapto)propionate (ISBMP)

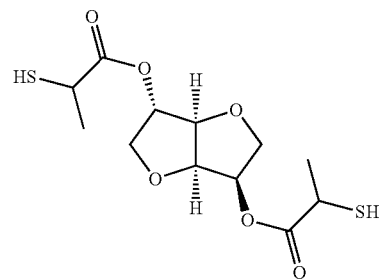 [SMILES: CC(S)C(=O)O[C@H]1CO[C@H]2[C@@H]1OC[C@H]2OC(=O)C(C)S]

A mixture of isosorbide (60.90 grams, 0.42 moles), 2-mercaptopropionic acid (96.00 g, 0.90 moles), toluene (300 mL), and methane sulfonic acid (1.00 g, 10 mmoles) was heated to reflux. Water was separated from the toluene/water azeotrope using a Dean Stark distillation trap. After 24 hours at reflux, a total of 15 mL of water was collected in the trap. The reaction mixture was cooled and washed with saturated aqueous sodium bicarbonate (3×300 mL) and brine (100 mL). The solution was dried over magnesium sulfate and then concentrated under reduced pressure. A yellow oil was obtained as the product. (Yield: 116.23 grams).

Example 3

Isosorbide bis-(3-mercapto)propionate (ISTMP)

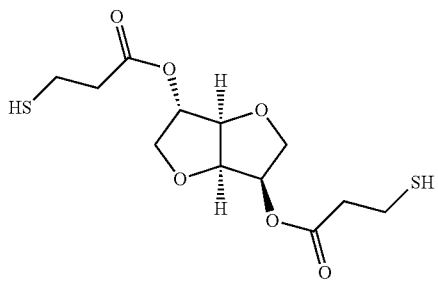 [SMILES: O=C(CCS)O[C@H]1CO[C@H]2[C@@H]1OC[C@H]2OC(=O)CCS]

A mixture of isosorbide (61.70 grams, 0.42 moles), 3-mercaptopropionic acid (97.00 grams, 0.91 moles), toluene (300 mL), and methane sulfonic acid (1.00 grams, 10 mmoles) was heated to reflux. Water was separated from the toluene/water azeotrope using a Dean Stark distillation trap. After 18 hours at reflux, a total of 15 mL of water was collected in the trap. The reaction mixture was cooled and washed with saturated aqueous sodium bicarbonate (3×300 mL) and brine (100 mL). The solution was dried over magnesium sulfate and then concentrated under reduced pressure. An orange oil was obtained as the product. (Yield: 125.93 grams).

Example 4

Bis-(3-mercaptopropyloxy)isosorbide (ISBMPE)

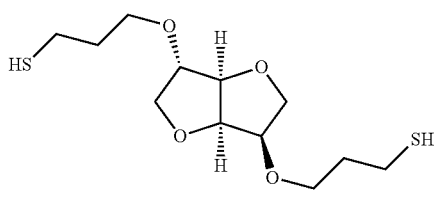 [SMILES: SCCCO[C@H]1CO[C@H]2[C@@H]1OC[C@H]2OCCCS]

A solution of sodium hydroxide (54.73 grams, 1.37 moles) in water (60 mL) was added dropwise over 2 hours to a stirred mixture of isosorbide (100.06 grams, 0.68 moles) and allyl bromide (238.50 grams, 1.98 moles). The temperature rose to 80° C. during the addition and then was held at 70° C. for 5 hours. The reaction mixture was diluted with water (120 mL) and then extracted with ethyl acetate (3×300 mL). The combined organic phases were washed with water and concentrated under vacuum. The crude oil product was distilled under vacuum (95 to 100° C. at 0.1 mmHg) to provide bis-allyloxy isosorbide as a colorless oil (117.31 grams).

A mixture of bis-allyloxy isosorbide (40.00 grams, 0.18 moles), thio-acetic acid (distilled prior to use, 34.66 grams, 0.46 moles), and 2,2'azobis(2-methylbutyronitrile) (0.10 grams) was stirred under nitrogen. The mixture quickly exothermed and was stirred at room temperature for 2 hours. The reaction mixture was diluted with ethyl acetate (200 mL) and then washed with aqueous sodium bicarbonate (100 mL). The organic phase was concentrated under vacuum to provide a yellow oil. The oil was mixed with a solution of sodium hydroxide (40.00 grams, 1.00 moles) and water (40 mL) and then heated to 90° C. for 4 hours. After cooling, the mixture was diluted with water (100 mL), and extracted with ethyl acetate (2×100 mL). The combined organic phases were washed with water (100 mL) and then concentrated under vacuum. A yellow oil was obtained (Yield: 46.44 grams).

Examples 5 to 8 and Comparative Example C1

Various mercaptans were reacted with sorbitol polyglycidyl polyether (ERISYS GE-60) as shown in Table 1. All formulations in this table contain equimolar amounts of the mercaptan and epoxy resin. The results from overlap shear (OLS) strength measurements of the cured compositions and the peak exotherm cure temperature (where available) are also included in Table 1.

TABLE 1

| | ERISYS GE-60 epoxy resin cured with various mercaptan compounds | | | |
|---|---|---|---|---|
| Example | Mercaptan | ERISYS GE-60 (grams) | Mercaptan (grams) | OLS (psi) | Cure Temperature (° C.) |
| 5 | ISTG | 1.00 | 0.73 | 3089 ± 78 | 98 |
| 6 | ISBMP | 1.00 | 0.83 | 2947 ± 85 | 111 |
| 7 | ISTMP | 1.00 | 0.83 | 2899 ± 168 | 137 |
| 8 | ISBMPE | 1.00 | 0.75 | 375 ± 90 | NM |
| C1 | EGDTG | 1.00 | 0.54 | 466 ± 39 | 122 |

NM—not measured

Examples 9 to 13

The mercaptan compound ISTG was also used as a curative in various epoxy resins as shown in Table 2. All formulations in this table contain equimolar amounts of the mercaptan and epoxy resin. The results from overlap shear strength measurements of the cured compositions are also included in Table 2.

TABLE 2

| | Various epoxy resins cured with ISTG | | | |
|---|---|---|---|---|
| Example | Epoxy Resin | Epoxy Resin (grams) | ISTG (grams) | OLS (psi) |
| 9 | EX-313 | 1.00 | 1.04 | 276 ± 80 |
| 10 | EX-512 | 1.00 | 0.87 | 1325 ± 180 |
| 11 | EX-521 | 1.00 | 0.76 | 1983 ± 155 |
| 12 | IDGE | 1.00 | 1.14 | 353 ± 108 |
| 13 | EPON 828 | 1.00 | 0.78 | 1073 ± 163 |

Examples 14 to 18

A curative package comprising amine and mercaptan was utilized in formulations as shown in Table 3. The epoxy resin was ERISYS GE-60, the mercaptan compound was ISTG, and the amine curative was 2-aminomethylfuran (FA). All formulations in this table contain equimolar amounts of epoxy resin and curative package, that is, the moles of epoxy resin are equal to the total moles of mercaptan and amine. The overlap shear strengths of various cured compositions were measured and are shown in Table 3.

TABLE 3

ERISYS GE-60 cured with ISTG and FA at various molar ratios

| Example | FA/ISTG molar ratio | ERISYS GE-60 (grams) | ISTG (grams) | FA (grams) | OLS (psi) |
|---|---|---|---|---|---|
| 14 | 9.0 | 1.50 | 0.11 | 0.34 | 3621 ± 204 |
| 15 | 4.0 | 1.50 | 0.23 | 0.30 | 4146 ± 375 |
| 16 | 2.3 | 1.50 | 0.34 | 0.26 | 2943 ± 91 |
| 17 | 1.0 | 1.50 | 0.57 | 0.19 | 1950 ± 259 |
| 18 | 0.3 | 1.50 | 0.85 | 0.09 | 1091 ± 96 |

Examples 19 to 33 and Comparative Examples C2 to C11

Various combinations of amines and mercaptans were also used for curing ERISYS GE-60 epoxy resin. Table 4 summarizes the compositions and overlap shear strength values for the resulting cured formulations. Comparative Examples C2 to C6 show compositions and OLS strengths of ERISYS GE-60 cured with amine hardeners alone. Comparative Examples C7 to C11 shows compositions using combinations of amine and EGDTG as the curative package for ERISYS GE-60. The molar ratio of amine to mercaptan was maintained at 4.0 in all formulations. In addition, all formulations in Table 4 contain equimolar amounts of epoxy resin and curative package, that is, the moles of epoxy resin are equal to the sum of the moles of mercaptan and amine.

TABLE 4

OLS strength of ERISYS GE-60, mercaptan, and various amines

| Example | Mercaptan | Amine | ERISYS GE-60 (grams) | Mercaptan (grams) | Amine (grams) | OLS Strength (psi) |
|---|---|---|---|---|---|---|
| C2 | — | FA | 1.00 | 0.00 | 0.25 | 3544 ± 34 |
| C3 | — | DHAA | 1.00 | 0.00 | 0.73 | 1912 ± 81 |
| C4 | — | TEKA | 1.00 | 0.00 | 0.71 | 1588 ± 117 |
| C5 | — | DTA | 1.00 | 0.00 | 0.70 | 2140 ± 13 |
| C6 | — | K54 | 1.00 | 0.00 | 1.36 | 298 ± 20 |
| C7 | EGDTG | FA | 1.00 | 0.11 | 0.20 | 2386 ± 92 |
| C8 | EGDTG | DHAA | 1.00 | 0.11 | 0.59 | 2210 ± 177 |
| C9 | EGDTG | TEKA | 1.00 | 0.11 | 0.57 | 1789 ± 75 |
| C10 | EGDTG | DTA | 1.00 | 0.11 | 0.56 | 2104 ± 298 |
| C11 | EGDTG | K54 | 1.00 | 0.11 | 1.09 | 900 ± 115 |
| 19 | ISTG | FA | 1.00 | 0.15 | 0.20 | 4146 ± 375 |
| 20 | ISTG | DHAA | 1.00 | 0.17 | 0.59 | 1523 ± 184 |
| 21 | ISTG | TEKA | 1.00 | 0.15 | 0.57 | 2273 ± 130 |
| 22 | ISTG | DTA | 1.00 | 0.15 | 0.56 | 2283 ± 41 |
| 23 | ISTG | K54 | 1.00 | 0.15 | 1.09 | 606 ± 7 |
| 24 | ISBMP | FA | 1.50 | 0.25 | 0.30 | 3766 ± 157 |
| 25 | ISBMP | DHAA | 1.50 | 0.25 | 0.88 | 2947 ± 85 |
| 26 | ISBMP | TEKA | 1.50 | 0.25 | 0.85 | 1922 ± 326 |
| 27 | ISBMP | DTA | 1.50 | 0.25 | 0.84 | 2378 ± 294 |
| 28 | ISBMP | K54 | 1.50 | 0.25 | 1.65 | 417 ± 68 |
| 29 | ISTMP | FA | 1.50 | 0.25 | 0.30 | 3632 ± 98 |
| 30 | ISTMP | DHAA | 1.50 | 0.25 | 0.88 | 2860 ± 166 |
| 31 | ISTMP | TEKA | 1.50 | 0.25 | 0.85 | 1763 ± 168 |
| 32 | ISTMP | DTA | 1.50 | 0.25 | 0.84 | 2424 ± 12 |
| 33 | ISTMP | K54 | 1.50 | 0.25 | 1.63 | 215 ± 7 |

Examples 34 to 39 and Comparative Example C12 to C14

Shown in Table 5 are overlap shear strength values for LDO cured with amines alone, and with amine/mercaptan curative packages at different equivalent ratios. Overlap shear test specimens were prepared as described above and were cured under ambient conditions for 24 hours and then for an additional 20 minutes at 180° C.

TABLE 5

OLS strength of LDO cured with amines and mercaptan (ISTG)

| Example | Amine | LDO (grams) | ISTG (grams) | Amine (grams) | ISTG/Amine mole ratio | OLS Strength (psi) |
|---|---|---|---|---|---|---|
| C12 | DTA | 0.25 | 0.00 | 0.41 | — | no cure (fluid) |
| C13 | TEKA | 0.25 | 0.00 | 0.41 | — | no cure (fluid) |
| C14 | K54 | 0.25 | 0.00 | 0.79 | — | no cure (fluid) |
| 34 | DTA | 0.25 | 0.22 | 0.20 | 1 | 64 |
| 35 | TEKA | 0.25 | 0.22 | 0.21 | 1 | 37 |
| 36 | K54 | 0.25 | 0.22 | 0.39 | 1 | 63 |
| 37 | DTA | 0.25 | 0.35 | 0.08 | 4 | 117 |
| 38 | TEKA | 0.25 | 0.35 | 0.08 | 4 | 209 |
| 39 | K54 | 0.25 | 0.35 | 0.13 | 4 | 114 |

Examples 40 to 42 and Comparative Examples C15 and C16

Table 6 shows the time to harden various curable compositions at room temperature.

TABLE 6

| Example | Mercaptan | Amine | ERISYS GE-60 (grams) | Mercaptan (grams) | Amine (grams) | Time to harden (minutes) |
|---|---|---|---|---|---|---|
| C15 | — | FA | 1.50 | 0.00 | 0.81 | >60 |
| C16 | EGDTG | FA | 1.50 | 0.40 | 0.19 | >30 |
| 40 | ISTG | FA | 1.50 | 0.57 | 0.19 | <1 |

TABLE 6-continued

| | | | Time to harden | | |
|---|---|---|---|---|---|
| Example | Mercaptan | A-mine | ERISYS GE-60 (grams) | Mercaptan (grams) | Amine (grams) | Time to harden (minutes) |
| 41 | ISBMP | FA | 1.50 | 0.62 | 0.19 | <5 |
| 42 | ISTMP | FA | 1.50 | 0.62 | 0.19 | 15 |

We claim:

1. A compound of Formula (I)

$$\text{HS-L-Y—O-Q-O—Y-L-SH} \quad (I)$$

wherein
each Y is independently a single bond or a carbonyl group;
each L is independently an alkylene or heteroalkylene; and
Q is a divalent group of Formula (I-1), Formula (I-2), or Formula (I-3)

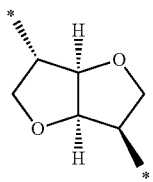
(I-1)

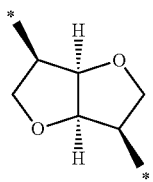
(I-2)

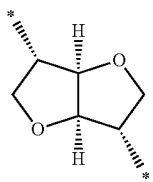
(I-3)

2. The compound of claim 1, wherein the compound is a liquid at 25° C.

3. The compound of claim 1, wherein the compound of Formula (I) is of Formula (II)

$$\text{HS-L-(CO)—O-Q-O—(CO)-L-SH} \quad (II).$$

4. The compound of claim 3, wherein the compound of Formula (II) is

HS—CH$_2$—(CO)—O-Q-O—(CO)—CH$_2$—SH,

HS—CH(CH$_3$)—(CO)—O-Q-O—(CO)—CH(CH$_3$)—SH, or

HS—CH$_2$CH$_2$—(CO)—O-Q-O—(CO)—CH$_2$CH$_2$—SH.

5. The compound of claim 1, wherein the compound of Formula (I) is of Formula (III)

$$\text{HS-L-O-Q-O-L-SH} \quad (III).$$

6. The compound of claim 5, wherein the compound of Formula (III) is

HS—CH$_2$CH$_2$CH$_2$—O-Q-O—CH$_2$CH$_2$CH$_2$—SH.

7. A curable composition comprising:
a) an epoxy resin; and
b) a first curing agent of Formula (I)

$$\text{HS-L-Y—O-Q-O—Y-L-SH} \quad (I)$$

wherein
each Y is independently a single bond or a carbonyl group;
each L is independently an alkylene or heteroalkylene; and
Q is a divalent group selected from Formula (I-1), Formula (I-2), or Formula (I-3)

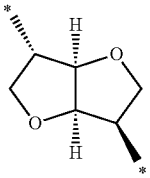
(I-1)

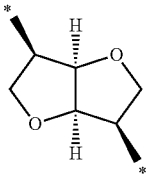
(I-2)

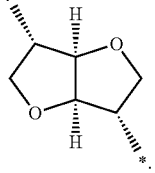
(I-3)

8. The curable composition of claim 7, further comprising a second curing agent comprising (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

9. The curable composition of claim 7, wherein the first curing agent of Formula (I) is of Formula (II)

$$\text{HS-L-(CO)—O-Q-O—(CO)-L-SH} \quad (II).$$

10. The curable composition of claim 7, wherein the first curing agent of Formula (I) is of Formula (III)

$$\text{HS-L-O-Q-O-L-SH} \quad (III).$$

11. The curable composition of claim 7, wherein the curable composition has a first part comprising the epoxy resin and a second part comprising the compound of Formula (I).

12. An article comprising a first substrate and a cured composition positioned adjacent to the first substrate, the cured composition comprising a reaction product of a curable composition comprising:
a) an epoxy resin; and
b) a first curing agent of Formula (I)

$$\text{HS-L-Y—O-Q-O—Y-L-SH} \quad (I)$$

wherein
each Y is independently a single bond or a carbonyl group;
each L is independently an alkylene or heteroalkylene; and
Q is a divalent group of Formula (I-1), Formula (I-2), or Formula (I-3)

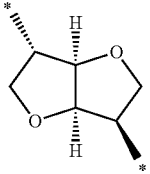
(I-1)

-continued

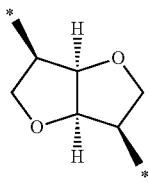
(I-2)

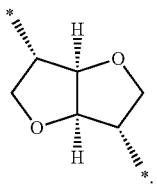
(I-3)

13. The article of claim 12, wherein the first curing agent of Formula (I) is of Formula (II)

HS-L-(CO)—O-Q-O—(CO)-L-SH  (II).

14. The article of claim 12, wherein the first curing agent of Formula (I) is of Formula (III)

HS-L-O-Q-O-L-SH  (III).

15. The article of claim 12, wherein the curable composition further comprises a second curing agent comprising (a) an amine compound having at least one primary amino group or at least one secondary amino group, (b) an imidazole, imidazoline, or salt thereof, (c) a phenol substituted with at least one group selected from a tertiary amino, secondary or tertiary alkyl, nitro, halo, hydroxyl, or combination thereof, (d) a bisphenol, (e) an anhydride, (f) a carboxylic acid, (g) a mercaptan, or (h) a mixture thereof.

* * * * *